(12) United States Patent
Kitaoka et al.

(10) Patent No.: US 7,459,697 B2
(45) Date of Patent: Dec. 2, 2008

(54) FLUORESCENCE MEASURING EQUIPMENT

(75) Inventors: Yasuo Kitaoka, Ibaraki (JP); Kazuhisa Yamamoto, Takatsuki (JP)

(73) Assignee: Panasonic Corporation, Osaka (JP)

( * ) Notice: Subject to any disclaimer, the term of this patent is extended or adjusted under 35 U.S.C. 154(b) by 250 days.

(21) Appl. No.: 10/518,136

(22) PCT Filed: Dec. 10, 2003

(86) PCT No.: PCT/JP03/15822

§ 371 (c)(1),
(2), (4) Date: Aug. 11, 2005

(87) PCT Pub. No.: WO2004/063730

PCT Pub. Date: Jul. 29, 2004

(65) Prior Publication Data

US 2006/0071179 A1    Apr. 6, 2006

(30) Foreign Application Priority Data

Jan. 16, 2003 (JP) .............................. 2003-008789

(51) Int. Cl.
*G01N 21/64* (2006.01)

(52) U.S. Cl. .................................. 250/458.1

(58) Field of Classification Search ............... 250/458.1
See application file for complete search history.

(56) References Cited

U.S. PATENT DOCUMENTS 5,773,828 A    6/1998    Akiyama et al.

2002/0093642 A1 *  7/2002  Eyolfson .................. 356/72
2005/0001175 A1 *  1/2005  White .................. 250/458.1

FOREIGN PATENT DOCUMENTS

| JP | 6-317526 | 11/1994 |
|---|---|---|
| JP | 06-317526 | * 11/1994 |
| JP | 7-270718 | 10/1995 |
| JP | 9-53991 | 2/1997 |
| JP | 2000-246227 | 9/2000 |
| JP | 2000-304699 | 11/2000 |
| JP | 2001-124696 | 5/2001 |
| JP | 2001-147374 | 5/2001 |
| JP | 2002-181706 | 6/2002 |
| JP | 2002-350732 | 12/2002 |

* cited by examiner

*Primary Examiner*—David P Porta
*Assistant Examiner*—Mindy Vu
(74) *Attorney, Agent, or Firm*—Hamre, Schumann, Mueller & Larson, P.C.

(57) ABSTRACT

A measuring substance (2) is excited by light emitted from a light source (1), fluorescence generated from the substance (2) is directed to transmission-type band-pass filters (4, 6, 8) sequentially, and light having a specific wavelength that has passed through the band-pass filters (4, 6, 8) is detected by light-receiving portions (5, 7, 9). Differences or relative ratios between the signal strengths detected by the respective light-receiving portions (5, 7, 9) are measured to determine a peak wavelength of the fluorescence spectrum, thus identifying the substance (2). With this configuration, a fluorometer can achieve a small size, low cost, and short-time detection.

5 Claims, 6 Drawing Sheets

FLUORESCENCE MEASURING EQUIPMENT

TECHNICAL FIELD

The present invention relates to a fluorometer used in the field of optical application measurement.

BACKGROUND ART

The structural analysis of a substance can be performed in such a manner that pigments or the like are fixed to the substance (e.g., protein), the substance is then excited by light, and the spectrum of fluorescence emitted from the substance is observed to evaluate the structure or behavior of the substance. Moreover, when rare-earth elements or the like are mixed with various base materials such as plastic and inorganic materials, fluorescence is observed by excitation of the base materials with light. Any change in a base material also changes the observed fluorescence spectrum. Therefore, the structure or the like of a base material can be analyzed by analyzing the fluorescence spectrum.

For the evaluation of a fluorescence spectrum, a measuring substance is irradiated and excited generally using a halogen lamp or the like. The fluorescence observed is evaluated with a spectroscope. FIG. 6 shows the configuration of the spectroscope.

Fluorescence 42 from a measuring substance 40 that has been irradiated with excitation light 41 is converged to a slit 44 by a lens 43. The fluorescence passing through the slit 44 is collimated by a lens 45 and then is directed to a diffraction grating 46. Light 48 that is diffracted by the diffraction grating 46 and passes through a slit 47 is observed, and a fluorescence spectrum is determined in accordance with the intensity distribution of the light 48.

There is another method for analyzing a fluorescence spectrum obtained by excitation with an Ar gas laser or semiconductor laser. When fluorescence from a living body is observed by irradiating it with a red semiconductor laser having a wavelength of 660 nm, a narrow-band-pass filter is used to separate the fluorescence from the excitation light because the fluorescence peak is 670 nm (e.g., Japanese Patent No. 3291898).

In the conventional configuration, a semiconductor layer, a gas laser, or the like is used as an excitation laser for exciting a substance, and the intensity of fluorescence generated from the substance is evaluated. However, such detection has disadvantages in that, e.g., when a plastic material contains rare earth, a slight structural change of the plastic material cannot be observed precisely.

In a detection system, the resultant fluorescence spectrum is diffracted by a reflection-type grating, and then is observed and detected by a CCD camera or the like. The use of a reflection-type grating in a spectral system increases the size of the device and causes a problem of stability. Moreover, the detection system including a CCD camera is expensive, and a long detection time is required to analyze the resultant fluorescence spectrum.

DISCLOSURE OF INVENTION

Therefore, with the foregoing in mind, it is an object of the present invention to provide a fluorometer that can achieve high-precision and high-speed detection.

A first fluorometer of the present invention detects the intensity of fluorescence generated from a substance that is excited by light emitted from a light source. Intensities P1, P2, ..., Pn of the fluorescence are detected respectively in n (n is an integer of not less than 2) limited wavelength regions λ1, λ2, ..., λn of the fluorescence.

A second fluorometer of the present invention detects the intensity of fluorescence generated from a substance that is excited by light emitted from a light source. The fluorometer includes n (n is an integer of not less than 2) narrow-band-pass filters for transmitting light in different limited wavelength regions of the fluorescence, and n light-receiving portions having one-to-one correspondence with the n narrow-band-pass filters. An intensity P1 of fluorescence transmitted through a first narrow-band-pass filter is detected by a first light-receiving portion. Fluorescence reflected from an (n−1)-th narrow-band-pass filter is allowed to enter an n-th narrow-band-pass filter, and an intensity Pn of fluorescence transmitted through the n-th narrow-band-pass filter is detected by an n-th light-receiving portion.

A third fluorometer of the present invention detects the intensity of fluorescence generated from a substance that is excited by light emitted from a light source. The fluorometer includes n (n is an integer of not less than 2) narrow-band reflection-type notch filters for reflecting light in different limited wavelength regions of the fluorescence, and n light-receiving portions having one-to-one correspondence with the n narrow-band reflection-type notch filters. An intensity P1 of fluorescence reflected from a first narrow-band reflection-type notch filter is detected by a first light-receiving portion. Fluorescence transmitted through an (n−1)-th narrow-band reflection-type notch filter is allowed to enter an n-th narrow-band reflection-type notch filter, and an intensity Pn of fluorescence reflected from the n-th narrow-band reflection-type notch filter is detected by an n-th light-receiving portion.

BEST MODE FOR CARRYING OUT THE INVENTION

The first to third fluorometers of the present invention detect the intensity of light in a plurality of limited wavelength regions of the fluorescence that is generated from a measuring substance by photoexcitation. Therefore, even a slight change in structure of the substance can be detected with high precision in a short time.

In the first to third fluorometers of the present invention, it is preferable that a relative ratio or a difference between the detected intensities P1, P2, ..., Pn of the fluorescence is determined. With this configuration, a peak wavelength and/or wavelength width of a spectrum of the fluorescence generated from the substance can be detected easily.

In the first to third fluorometers of the present invention, the light source is preferably a light-emitting diode or wavelength-variable semiconductor laser. With this configuration, the intensity of the fluorescence generated from the substance can be improved, thereby increasing the measurement accuracy.

In the first to third fluorometers of the present invention, a rare-earth element is preferably added to the substance. With this configuration, the intensity of the fluorescence generated from the substance can be improved, thereby increasing the measurement accuracy.

In the first to third fluorometers of the present invention, it is preferable that a wavelength width of a spectrum of the fluorescence generated from the substance is detected by comparing the detected intensities P1, P2, . . . , Pn of the fluorescence. With this configuration, a slight change in structure of the substance can be detected with high precision based on a difference between the wavelength widths even if the peak wavelength of the spectrum of the fluorescence generated from the substance is the same.

In the third fluorometer of the present invention, it is preferable that the narrow-band reflection-type notch filter includes a pair of glass substrates and a photopolymer arranged between the pair of glass substrates, and a periodic change in refractive index of the photopolymer occurs in its thickness direction. With this configuration, the reflection-type notch filter can be small and simple in structure.

Hereinafter, a fluorometer of the present invention will be described with reference to the drawings.

Embodiment 1

Embodiment 1 of the present invention describes a method for identifying a material that includes a fluorescent material by evaluating a fluorescence spectrum of the material with a plurality of light-receiving portions.

Figure 1:
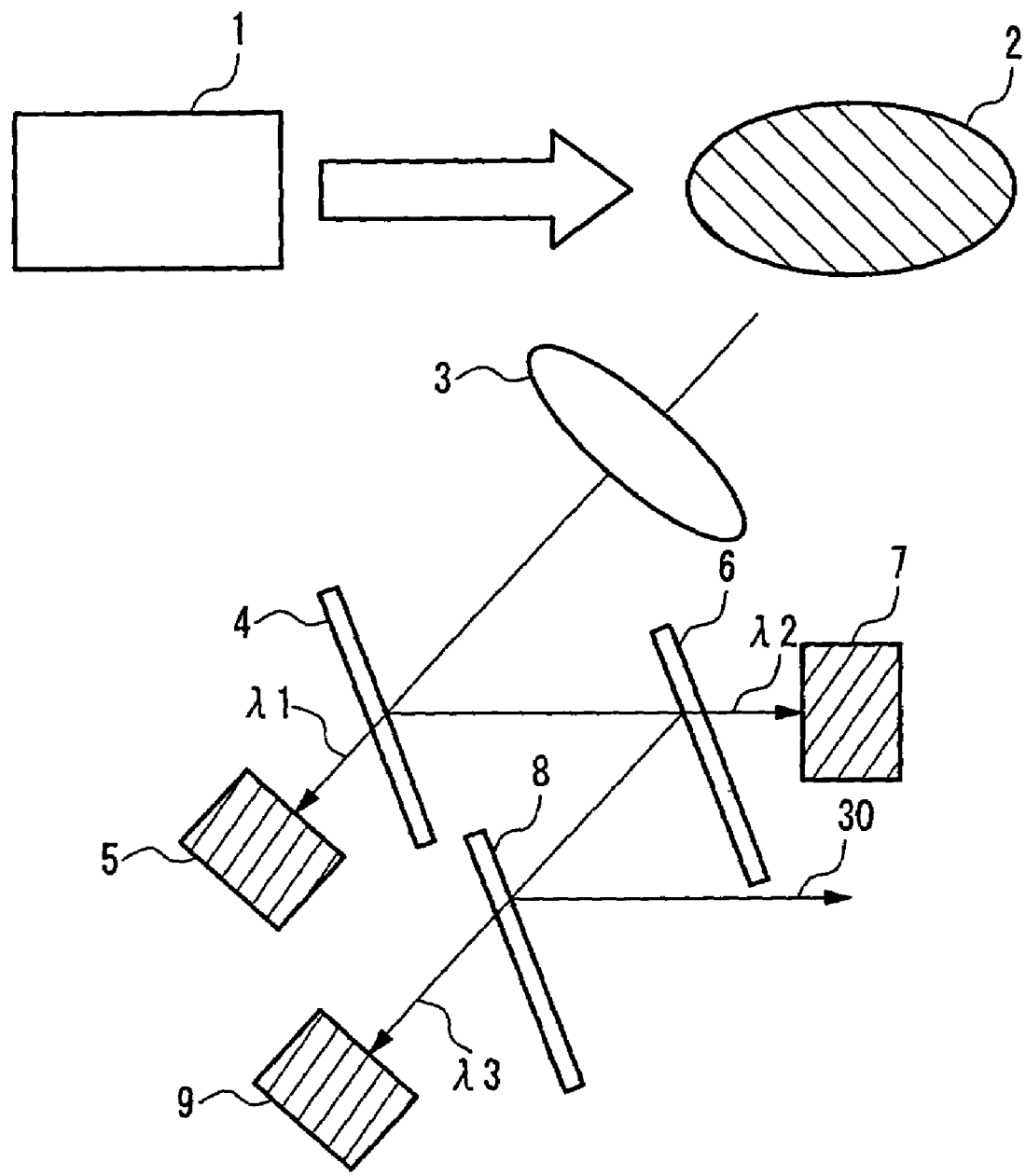
FIG. 1 shows the schematic configuration of a fluorometer of Embodiment 1 of the present invention.

FIG. 1 shows a fluorometer of Embodiment 1 of the present invention. A substance 2 is irradiated using a white LED (light emitting diode) 1 of a visible region. The fluorescence generated from the substance 2 is collimated by a lens 3, and transmitted light $\lambda 1$ of a first band-pass filter 4 is detected by a first photodetector 5. Reflected light of the first band-pass filter 4 is directed to a second band-pass filter 6, and transmitted light $\lambda 2$ of the second band-pass filter 6 is detected by a second photodetector 7. Further, reflected light of the second band-pass filter 6 is directed to a third band-pass filter 8, and transmitted light $\lambda 3$ of the third band-pass filter 8 is detected by a third photodetector 9. Reference numeral 30 denotes reflected light of the third band-pass filter 8. In this embodiment, three band-pass filters and three photodetectors are used. However, four or more band-pass filters and photodetectors can provide higher-precision detection.

Figure 2A:
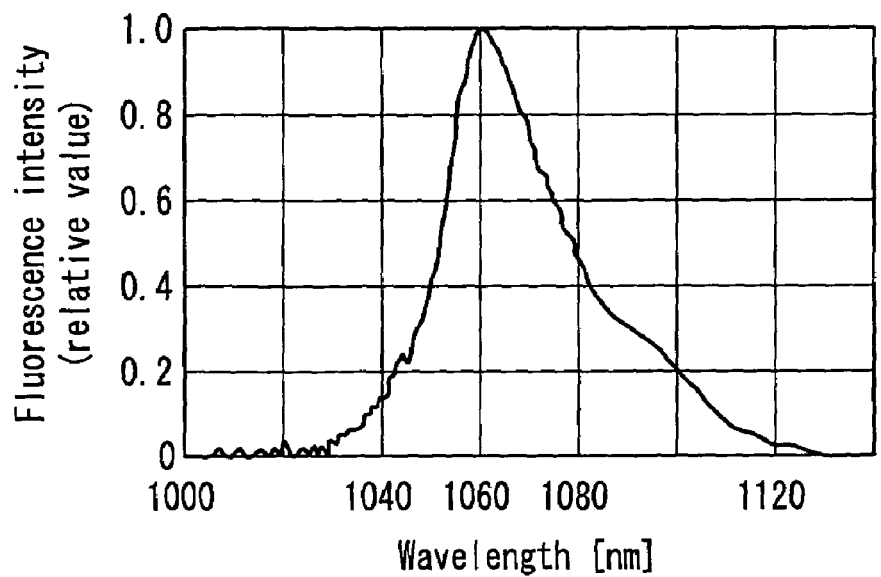
FIGS. 2A and 2B show the fluorescence spectra of silicate glass and phosphate glass, respectively.
Figure 2B:
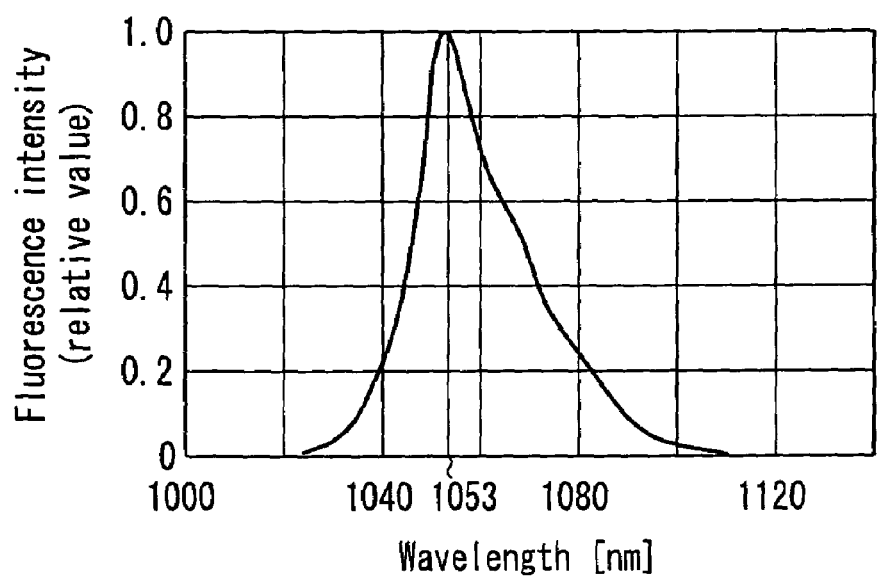

For example, when Nd (a typical rare-earth element) is added to glass, the fluorescence spectra of silicate glass and phosphate glass are shown in FIGS. 2A and 2B, respectively. Although the same Nd is added, the graphs show that the fluorescence spectra have different characteristics.

The following is an example that uses the fluorometer with the configuration in FIG. 1 to distinguish between two glass materials. The silicate glass and the phosphate glass absorb light in wavelength ranges of 580 nm and 750 to 880 nm. The glass materials were excited by the white LED. In this example, a band-pass filter having a transmittance of 70% and a full width at half maximum in transmission spectrum of 0.2 nm was used as the band-pass filters 4, 6, and 8. The peak wavelength of the transmission spectrum can be varied by changing the incident angle of light entering each of the band-pass filters 4, 6, and 8. The transmission peak wavelengths of the first, second and third band-pass filters 4, 6, and 8 were set to 1050 nm, 1060 nm, and 1070 nm, respectively.

Since the band-pass filters 4, 6, and 8 had a transmittance of about 70%, the amounts of light detected by the second photodetector 7 and the third photodetector 9 were corrected by the amount corresponding to a transmission loss. By determining the relative ratios or differences between the signal strengths detected by the first, second, and third photodetectors 5, 7, and 9, the two materials can be distinguished. In this example, differences between the signal strengths (after correction) P1, P2, and P3 detected respectively by the first, second, and third photodetectors 5, 7, and 9 were determined. For the silicate glass, $P1-P2<0$ and $P2-P3>0$.

For the phosphate glass, $P1-P2>0$ and $P2-P3>0$.

Consequently, the fluorescence peak wavelength of the silicate glass was detected in the vicinity of 1060 nm (i.e., ranging from 1050 to 1070 nm). Thus, the result confirms that this can be used to distinguish the silicate glass from the phosphate glass.

As described above, a peak wavelength can be determined precisely by using the fluorometer of this embodiment that includes three band-pass filters and three light-receiving portions in accordance with differences or relative ratios between the fluorescence intensities detected by the respective light-receiving portions.

In the above example, the transmission peak wavelengths of the band-pass filters were set to 1050 nm, 1060 nm, and 1070 nm at intervals of 10 nm. When the wavelength interval is about 1 nm, a narrower fluorescence spectrum can be detected with high precision.

In this embodiment, a peak wavelength of the fluorescence spectrum is detected. The configuration including the band-pass filters of this embodiment also can detect a wavelength width of the fluorescence spectrum. For example, when the same rare-earth element is mixed with different base materials, the peak wavelength of the fluorescence spectrum may be the same, while the wavelength width (full width at half maximum) may be different. In such a case, if the peak wavelength is P2, the evaluation of the fluorescence spectrum using the configuration of this embodiment shows that both materials are represented by $P1-P2<0$ and $P2-P3<0$.

However, the wavelength width of the fluorescence spectrum can be detected based on the relationship of P1 and P3 with respect to P2. In other words, the wavelength width decreases as the signal strengths P1 and P3 decrease, and the wavelength width increases as the signal strengths P1 and P3 increase. Thus, the fluorometer including a plurality of band-pass filters and photodetectors of this embodiment can measure not only a peak wavelength but also a wavelength width of the fluorescence spectrum, so that the fluorescence spectrum can be detected with higher precision, and even a small difference in a base material can be recognized.

Embodiment 2

In Embodiment 1, a substance is identified by focusing on one peak wavelength of fluorescence generated from the substance, setting the transmission peak wavelengths of a plurality of band-pass filters to the one peak wavelength and wavelengths on both sides of the one peak wavelength, and measuring the intensities of light at these wavelengths simultaneously to determine a peak wavelength of the fluorescence. The fluorescence spectrum generally has two or more peak wavelengths. Accordingly, when the transmission peak wavelengths of a plurality of band-pass filters are set to the two or more peak wavelengths, and ratios between the signal strengths detected by the respective photodetectors are evaluated, a substance also can be identified.

For example, the fluorescence spectra of YAG and $YVO_4$ materials, each of which contains Nd, will be described below. Under excitation with light having a wavelength of about 809 nm, the fluorescence spectrum of YAG containing Nd (referred to as "Nd:YAG" in the following) has its peaks of 0.946 µm, 1.064 µm, and 1.319 µm, while the fluorescence spectrum of $YVO_4$ containing Nd (referred of as "Nd:$YVO_4$" in the following) has its peaks of 0.914 µm, 1.064 µm, and 1.342 µm. Although the same rare-earth element Nd is added, there is a difference in peak wavelengths between the fluorescence spectra obtained. This is a general phenomenon, indicating that the fluorescence spectrum depends on the relationship between the additive and the base material. Nd:YAG and Nd:$YVO_4$ can be distinguished by utilizing the fact that they are the same in a peak wavelength of 1.064 µm, but are different in the other peak wavelengths.

Figure 3:
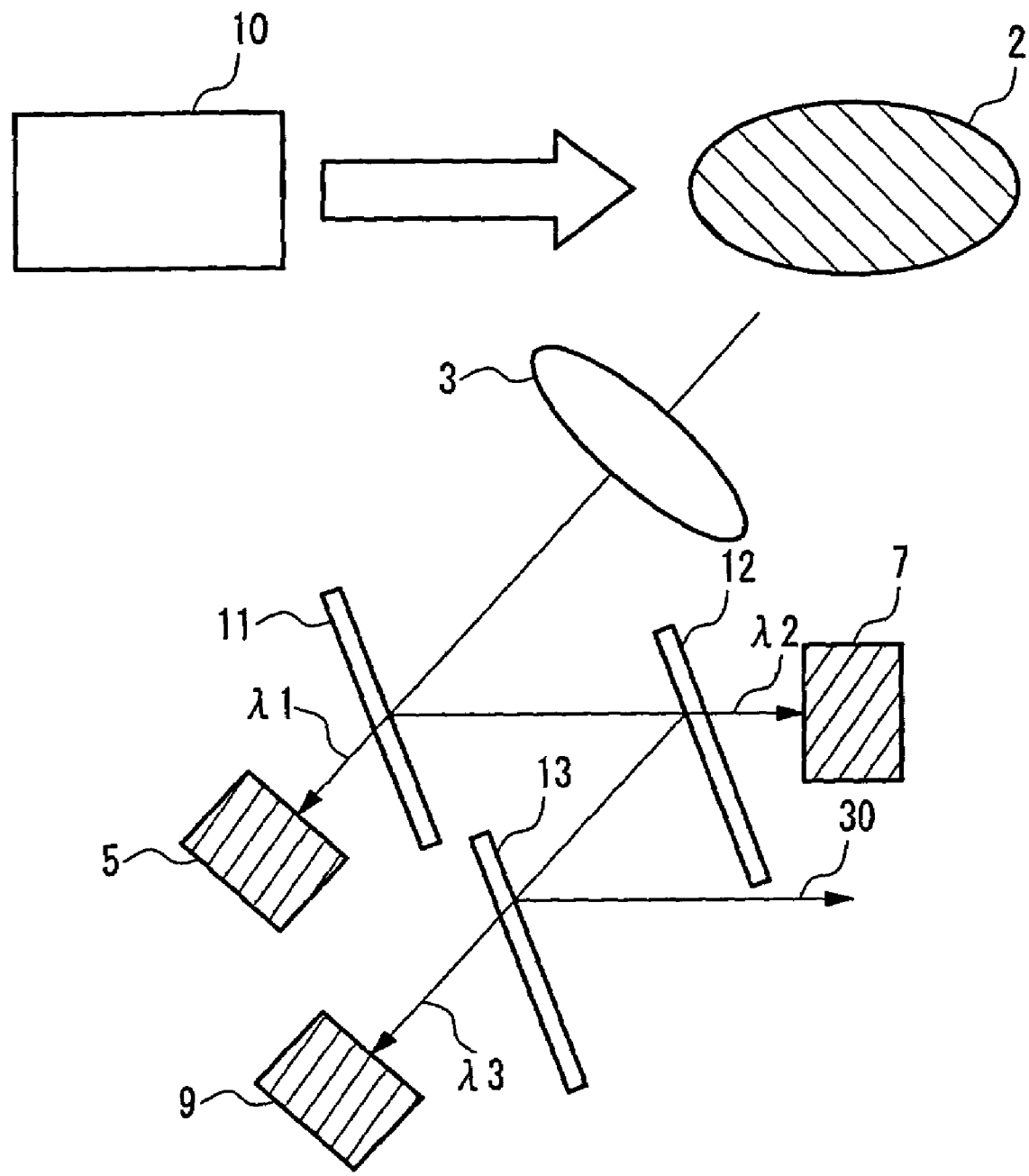
FIG. 3 shows the schematic configuration of a fluorometer of Embodiment 2 of the present invention.

FIG. 3 shows the schematic configuration of a fluorometer for distinguish Nd:YAG from Nd:$YVO_4$. The identical elements to those in FIG. 1 are denoted by the same reference numerals. In this example 2, a semiconductor laser 10 having a wavelength of 809 nm was used as an excitation light source. The transmission peak wavelengths of first, second, and third band-pass filters 11, 12, and 13 were set to 1064 nm, 946 nm, and 1319 nm, respectively. Since the band-pass filters 11, 12, and 13 had a transmittance of about 70%, the amounts of light detected by the second photodetector 7 and the third photodetector 9 were corrected by the amount corresponding to a transmission loss. When the intensity P2 of light transmitted through the second band-pass filter 12 and the intensity P3 of light transmitted through the third band-pass filter 13 are compared with the intensity P1 of light (1064 nm) transmitted through the first band-pass filter 11 as reference, the material can be identified more precisely. That is, differences or relative ratios between P1 and P2 and between P1 and P3 are determined and compared, thereby identifying the material immediately.

Embodiment 3

Embodiment 3 of the present invention describes a configuration that includes reflection-type notch filters instead of the transmission-type band-pass filters in Embodiment 1.

Figure 4:
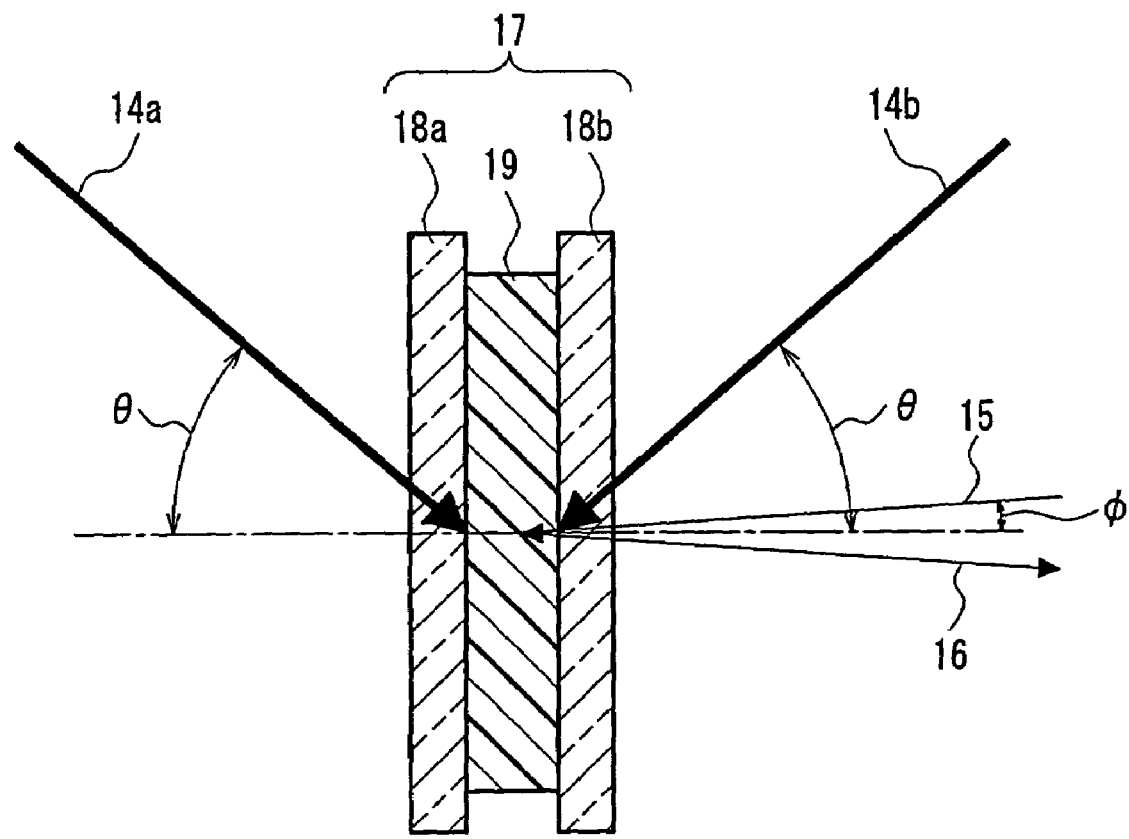
FIG. 4 shows the schematic configuration of a reflection-type notch filter.

As shown in FIG. 4, a notch filter 17 includes a first glass substrate 18a and a second glass substrate 18b that sandwich a photopolymer 19. The photopolymer 19 is formed on the first glass substrate 18a by spin coating in a thickness of about 1 mm. When rays of light 14a and 14b such as second harmonics (532 nm) of a YAG laser enter both sides of the notch filter 17, a periodic change in refractive index occurs in the thickness direction of the photopolymer 19 due to two-beam interference. A period d of the interference fringes (i.e., a change in refractive index) produced by the laser beams (wavelength λ) 14a and 14b, each entering at an incident angle θ (angle in the photopolymer), satisfies the relationship expressed by $\lambda/2 \cos \theta = d$.

Thus, the period d of the interference fringes increases as the incident angle θ becomes larger. In this example, the interference fringes with a period d of 532 nm were produced for θ=60 degrees. When light 15 having a wavelength of 1064 nm enters the notch filter 17 substantially perpendicular to the plane of incidence at an incident angle φ, diffracted light 16 is generated by Bragg diffraction. The notch filter 17 reflects (diffracts) only light having a specific wavelength in accordance with the incident angle φ, and thus can be used as a reflection-type filter. This reflection-type filter has angular dependence in which the wavelength of the diffracted light 16 is shorter as the incident angle φ of the light 15 entering the filter becomes larger.

Figure 5:
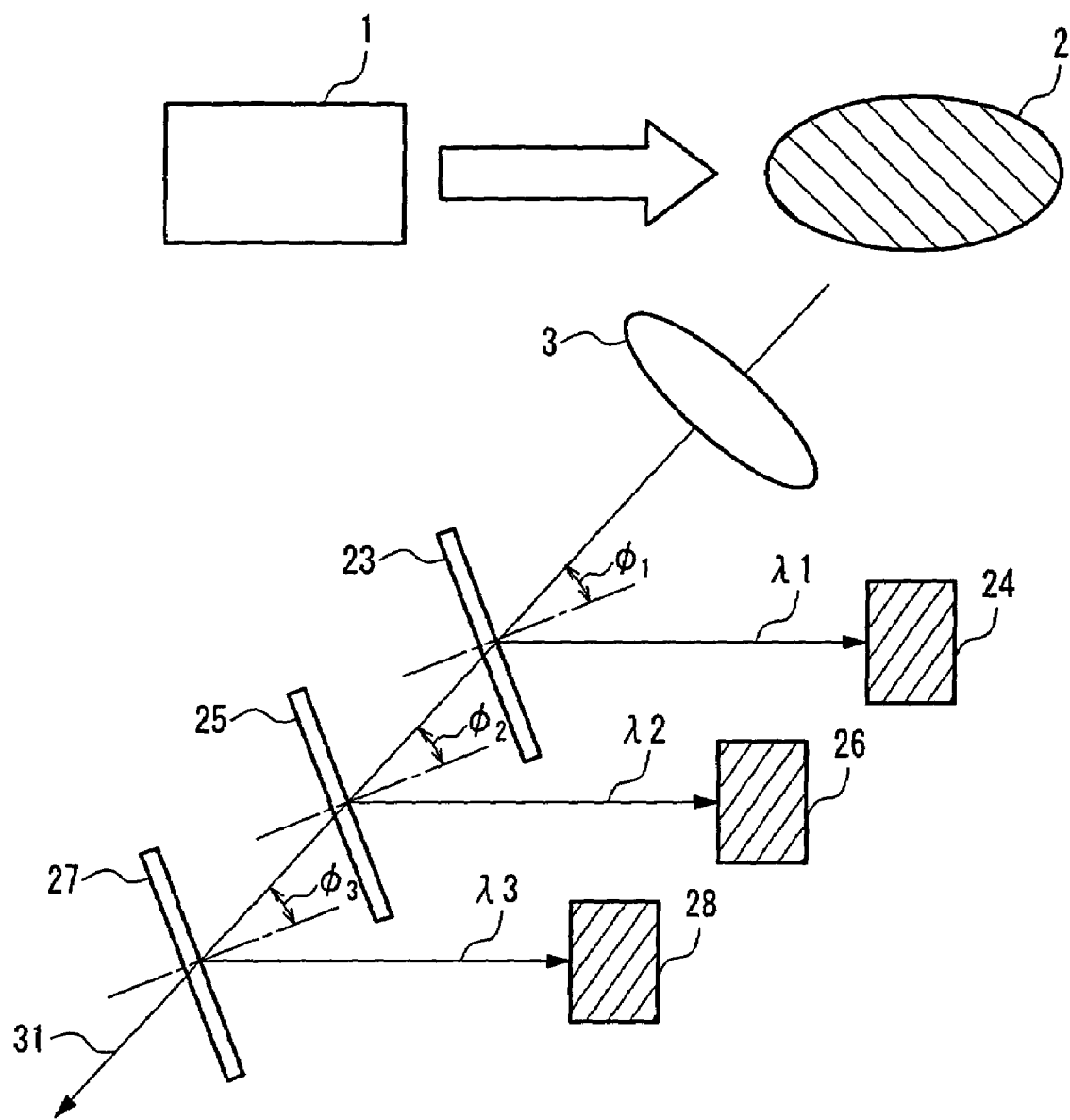
FIG. 5 shows the schematic configuration of a fluorometer of Embodiment 3 of the present invention.
Figure 6:
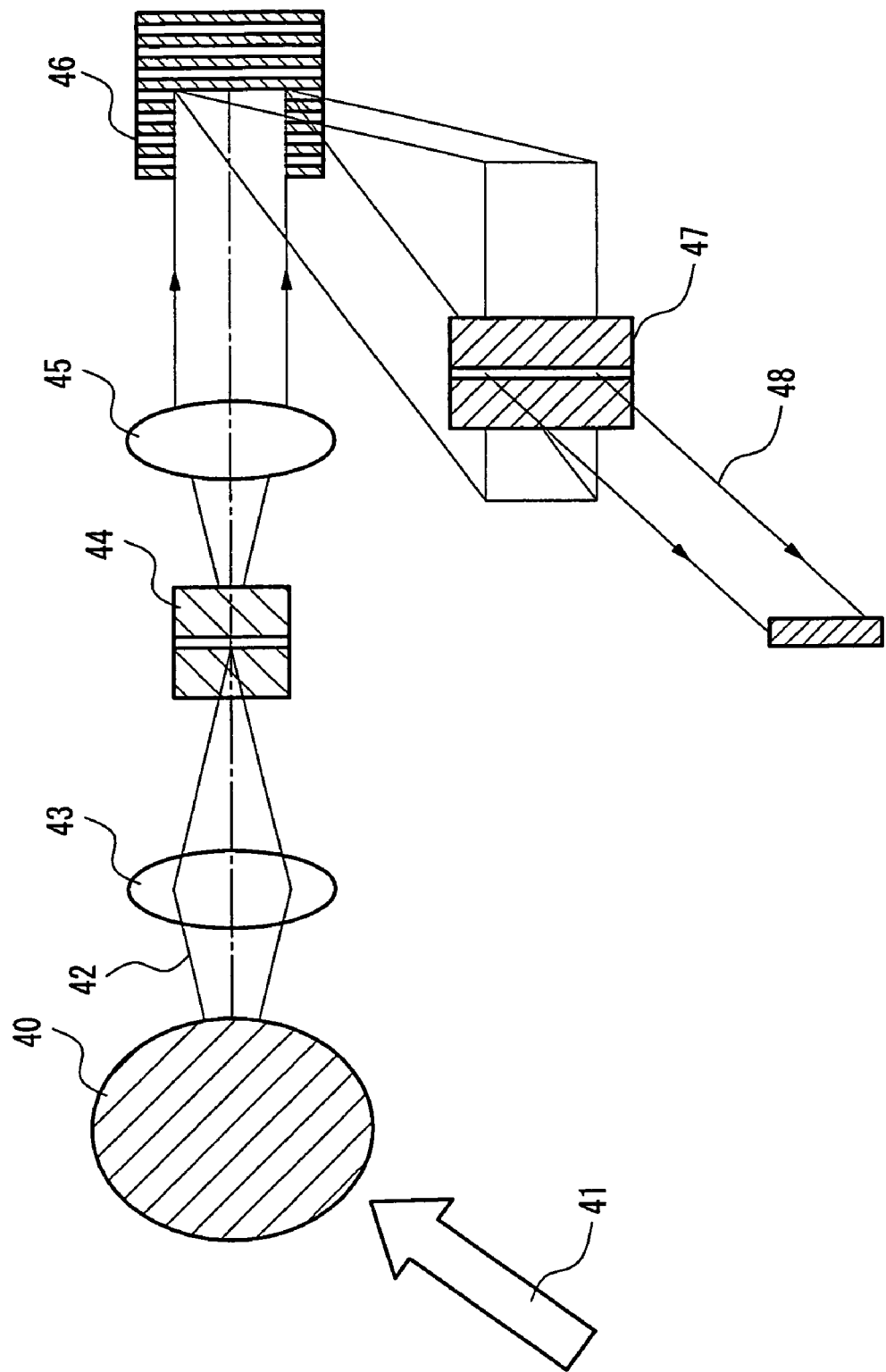
FIG. 6 shows the schematic configuration of a conventional spectroscope.

FIG. 5 shows the schematic configuration of a fluorometer including the above reflection-type notch filters. The identical elements to those in FIG. 1 are denoted by the same reference numerals. The following is an example that uses the fluorometer in FIG. 5 to distinguish between silicate glass and phosphate glass as described in Embodiment 1. First, reflection-type notch filters 23, 25, and 27 were prepared so that light in a wavelength range of 1060 nm is Bragg-diffracted when the incident angle φ is about 20 degrees by adjusting the incident angle θ responsible for the two-beam interference. Then, the incident angles $\phi_1$, $\phi_2$, and $\phi_3$ of light traveling from a lens 3 to the reflection-type notch filters 23, 25, and 27 were adjusted, and the reflection wavelengths of the reflection-type notch filters 23, 25, and 27 were set to 1050 nm, 1060 nm, and 1070 nm, respectively. Fluorescence generated from a substance 2 that has been excited by a white LED 1 is collimated by the lens 3 and directed to the first notch filter 23, and reflected light λ1 of the first notch filter 23 is detected by a first photodetector 24. Transmitted light of the first notch filter 23 is directed to the second notch filter 25, and reflected light λ2 of the second notch filter 25 is detected by a second photodetector 26. Further, transmitted light of the second notch filter 25 is directed to the third notch filter 27, and reflected light λ3 of the third notch filter 27 is detected by a third photodetector 28. Reference numeral 31 denotes transmitted light of the third notch filter 27. The amounts of light detected by the second photodetector 26 and the third photodetector 28 were corrected by the amount corresponding to a transmission loss of the reflection-type notch filters. Like Embodiment 1, the silicate glass and the phosphate glass were distinguished by determining relative ratios or differences between the signal strengths detected by the first, second and third photodetectors 24, 26, and 28.

In this embodiment, four or more reflection-type notch filters and photodetectors may be used to provide higher-precision detection.

In Embodiments 1 to 3, inorganic materials are used as a base material. However, the same effect also can be obtained by using organic materials such as plastic and protein. Although a pigment or the like may be used as an additive for generating fluorescence, rare-earth elements are preferred. In particular, when a material is identified or analyzed with a fluorometer of the present invention, the absorption or emission spectrum is narrow. Therefore, the addition of rare-earth elements can provide a significant effect.

Because of the narrow absorption or emission spectrum, it is preferable that a light-emitting diode or wavelength-variable semiconductor laser is used as an excitation light source to achieve efficient excitation and higher fluorescence intensity.

As described above, the fluorescence spectra differ depending on base materials even if the same rare-earth element is added to the base materials. The materials can be distinguished easily when there is a considerable difference between the fluorescence spectra. In some cases, however, a change in fluorescence spectrum may be small. According to the above embodiments, it is possible to make a precise distinction by comparing a plurality of peak intensities of a fluorescence spectrum. Moreover, the distinction accuracy can be improved further by increasing the number of peak intensities detected.

A fluorometer of the present invention that includes narrow-band-pass filters (or narrow-band reflection-type notch filters) and light-receiving portions has the advantages of a simple configuration, low cost, and quick measurement. Therefore, it is expected that the fluorometer will be used widely in the field of consumer application to identify general products of plastics or the like containing a fluorescent material. Compared with a grating used in a conventional spectroscope, the narrow-band-pass filter and the narrow-band reflection-type notch filter can provide a smaller size and higher stability for mechanical vibration, so that a more practical fluorometer can be achieved.

As described above, in the present invention, fluorescence generated by photoexcitation is detected in limited wavelength ranges, and the intensities detected are compared, so that a substance that emits the fluorescence can be identified precisely. Moreover, the present invention uses narrow-band-pass filters (or narrow-band reflection-type notch filters) and photodetectors, and thus can provide a simple high-speed fluorometer.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

The invention claimed is:

1. A system for detecting intensity of fluorescence generated from a substance that is excited by light, comprising:
  a single light source emitting light having one wavelength;
  a fluorometer, comprising:
    n (n is an integer of not less than 2) narrow-band-pass filters for transmitting light in different limited wavelength regions of the fluorescence, and
    n light-receiving portions having one-to-one correspondence with the n narrow-band-pass filters,
    wherein the n narrow-band-pass filters are arranged to each have a different incident angle of light,
    wherein the n narrow-band-pass filters share a similar transmittance configuration;
    wherein an intensity P1 of fluorescence transmitted though a first narrow-band-pass filter is detected by a first light-receiving portion, and
    wherein fluorescence reflected from an (n−1)-th narrow-band-pass filter is allowed to enter an n-th narrow-band-pass filter, and an intensity Pn of fluorescence transmitted through the n-th narrow-band-pass filter is detected by an n-th light-receiving portion, and
    wherein a relative ratio or a difference between the intensities P1, P2 . . . , Pn of the fluorescence detected respectively by the n light-receiving portions is determined to detect a wavelength width of a spectrum of the fluorescence.

2. The system according to claim 1, wherein the light source is a light-emitting diode.

3. The system according to claim 1, wherein a rare-earth element is added to the substance.

4. The system according to claim 1, wherein a wavelength width of a spectrum of the fluorescence generated from the substance is detected by comparing the detected intensities P1, P2, . . . , Pn of the fluorescence.

5. The system according to claim 1, wherein differences between the wavelength width of the spectrum of the fluorescence are distinguished with one or more substances with different fluorescence spectra.

* * * * *